(12) United States Patent
Power et al.

(10) Patent No.: US 9,192,407 B2
(45) Date of Patent: *Nov. 24, 2015

(54) WIRE GUIDES AND ANCHORS FOR ENDOSCOPY

(71) Applicant: Covidien LP, Mansfield, MA (US)

(72) Inventors: James M Power, Madison, CT (US); Frank Viola, Sandy Hook, CT (US); Russell Heinrich, Madison, CT (US)

(73) Assignee: Covidien LP, Mansfield, MA (US)

( * ) Notice: Subject to any disclaimer, the term of this patent is extended or adjusted under 35 U.S.C. 154(b) by 86 days.

This patent is subject to a terminal disclaimer.

(21) Appl. No.: 14/074,796

(22) Filed: Nov. 8, 2013

(65) Prior Publication Data

US 2014/0135654 A1  May 15, 2014

Related U.S. Application Data

(63) Continuation of application No. 13/404,184, filed on Feb. 24, 2012, now Pat. No. 8,586,865.

(60) Provisional application No. 61/466,495, filed on Mar. 23, 2011.

(51) Int. Cl.
*H02G 3/04* (2006.01)
*A61B 17/34* (2006.01)
(Continued)

(52) U.S. Cl.
CPC ......... *A61B 17/3423* (2013.01); *A61B 1/00087* (2013.01); *A61B 1/00096* (2013.01); *A61B 1/00154* (2013.01); *A61B 1/012* (2013.01); *A61B 1/04* (2013.01); *A61B 1/07* (2013.01); *A61B 1/3132* (2013.01); *A61B 5/6852* (2013.01); *A61B 17/0218* (2013.01); *A61B 17/3421* (2013.01); *A61B 19/5202* (2013.01); *A61B 19/5212* (2013.01); *A61B 2017/00283* (2013.01); *A61B 2017/00876* (2013.01);
(Continued)

(58) Field of Classification Search
USPC ................................................ 174/68.1, 68.3
See application file for complete search history.

(56) References Cited

U.S. PATENT DOCUMENTS

| 4,625,938 A | 12/1986 | Brown |
| 4,710,819 A | 12/1987 | Brown |

(Continued)

FOREIGN PATENT DOCUMENTS

| DE | 10004264 A1 | 8/2001 |
| EP | 2116201 A1 | 11/2009 |
| EP | 2305150 A1 | 4/2011 |
| JP | 2004-180858 A | 7/2004 |
| WO | WO-2010083480 A2 | 7/2010 |

OTHER PUBLICATIONS

European Search Report for corresponding EP12160861, date of mailing is Jun. 13, 2012.

*Primary Examiner* — Dhirubhai R Patel

(57) ABSTRACT

A wire guide system is provided for use during a endoscopic surgical procedures. The wire guide system includes a cylindrical shaft having a hollow chamber along a longitudinal axis of the cylindrical shaft, a flange fit disposed around the cylindrical shaft and a seal disposed around the cylindrical shaft and abutting the flange. The system may also include an anchor affixed to the cylindrical shaft and having an aperture from which at least one of a sensor, a light, a camera, tissue and/or organs may be suspended therefrom and at least one cable extending from one end of the cylindrical shaft to another end of the cylindrical shaft through the hollow chamber.

9 Claims, 5 Drawing Sheets

(51) Int. Cl.
- *A61B 1/00* (2006.01)
- *A61B 1/012* (2006.01)
- *A61B 1/313* (2006.01)
- *A61B 1/04* (2006.01)
- *A61B 1/07* (2006.01)
- *A61B 5/00* (2006.01)
- *A61B 17/02* (2006.01)
- *A61B 19/00* (2006.01)
- *A61B 17/00* (2006.01)

(52) U.S. Cl.
CPC ... *A61B2017/3492* (2013.01); *A61B 2019/267* (2013.01); *A61B 2019/5483* (2013.01)

(56) References Cited

U.S. PATENT DOCUMENTS

| | | | |
|---|---|---|---|
| 5,224,426 | A | 7/1993 | Rodnunsky et al. |
| 5,431,152 | A * | 7/1995 | Flam et al. ............ 600/120 |
| 5,941,818 | A | 8/1999 | Hori et al. |
| 6,309,397 | B1 | 10/2001 | Julian et al. |
| 6,325,755 | B1 | 12/2001 | Bushek et al. |
| 7,034,221 | B2 | 4/2006 | Johnston et al. |
| 8,586,865 | B2 | 11/2013 | Power et al. |
| 2007/0049794 | A1 | 3/2007 | Glassenberg et al. |
| 2009/0048611 | A1 | 2/2009 | Funda et al. |
| 2010/0228094 | A1 | 9/2010 | Ortiz et al. |

* cited by examiner

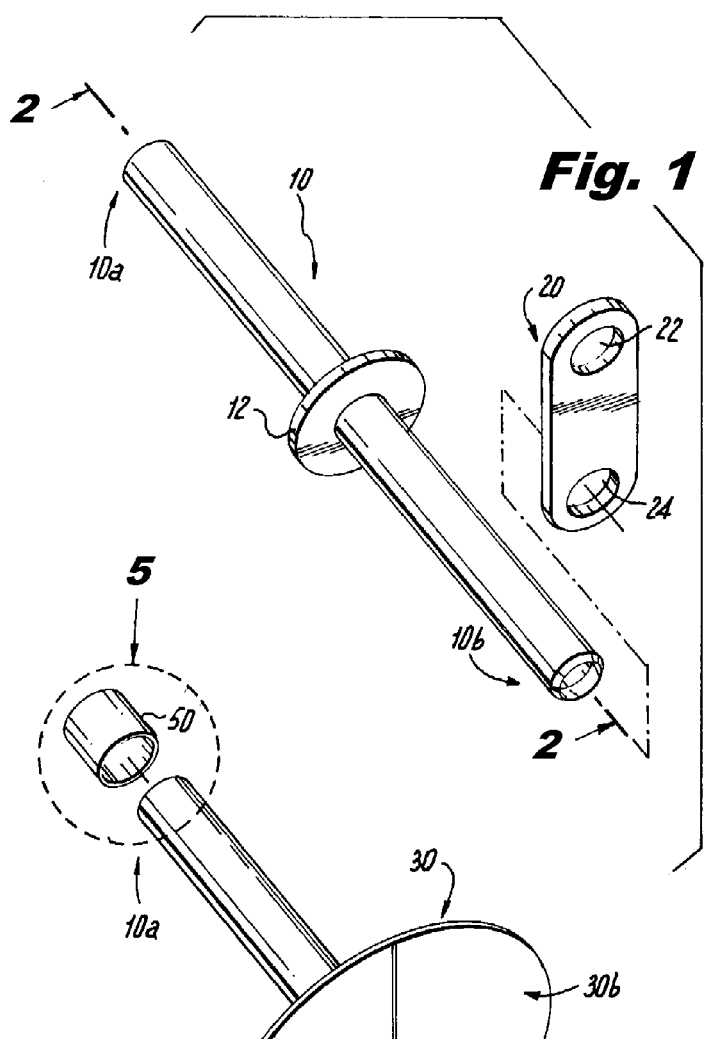
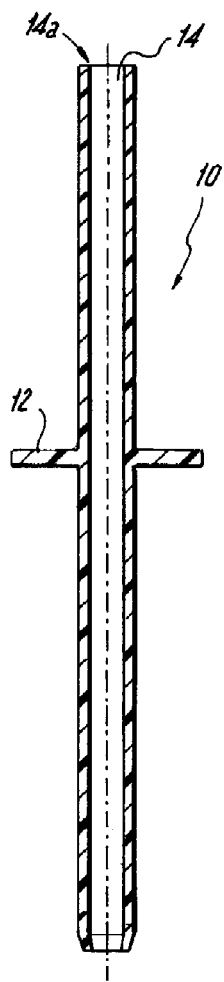
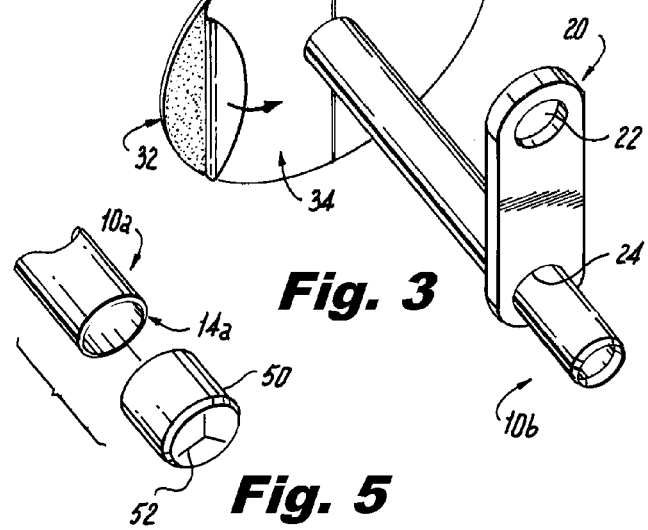
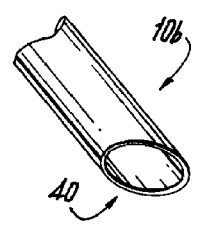
Fig. 1
Fig. 2
Fig. 3
Fig. 4
Fig. 5

WIRE GUIDES AND ANCHORS FOR ENDOSCOPY

CROSS REFERENCE TO RELATED APPLICATIONS

The present application is a Continuation Application of U.S. patent application Ser. No. 13/404,184 filed on Feb. 24, 2012, which claims the benefit of and priority to U.S. Provisional Application Ser. No. 61/466,495, now U.S. Pat. No. 8,586,865, filed on Mar. 23, 2011, the entire contents of which are incorporated herein by reference.

BACKGROUND

1. Technical Field

The present disclosure generally relates to the field of endoscopic surgery. More particularly, the present disclosure relates to apparatuses for providing power, data, illumination, and other wires and electrical connections into a body cavity.

2. Background of Related Art

Laparoscopy, also called minimally invasive surgery (MIS), is a modern surgical technique in which operations in the abdomen are performed through small incisions as compared to larger incisions needed in traditional surgical procedures. Laparoscopy provides a number of advantages versus open procedures that include reduced pain from infection and hemorrhaging and shorter recovery time.

The key element in laparoscopic surgery is the use of a laparoscope of which there are several types, for example: (1) a telescopic rod lens system, that is usually connected to a video camera (single chip or three chip), or (2) a digital laparoscope where the charge-coupled device is placed at the end of the laparoscope, eliminating the rod lens system or (3) a fiber optic bundle. A fiber optic cable system connected to a 'cold' light source (halogen or xenon) may also be attached to illuminate the operative field. The fiber optic cable system may be inserted through a 5 mm or 10 mm cannula to view the operative field. The abdomen is usually insufflated, or essentially blown up like a balloon, with carbon dioxide gas ($CO_2$). This elevates the abdominal wall above the internal organs like a dome to create a working and viewing space. $CO_2$ is used because it is common to the human body and can be absorbed by tissue and removed by the respiratory system. It is also non-flammable, which is important because electrosurgical devices are commonly used in laparoscopic procedures.

Known laparoscopy technologies are limited in scope and complexity due in part to 1) mobility restrictions resulting from using rigid tools inserted through access ports, and 2) limited visual feedback. That is, long rigid laparoscopic tools inserted through small incisions in the abdomen wall limit the surgeon's range of motion and therefore the complexity of the surgical procedures being performed. Similarly, using a 2-D image from a typically rigid laparoscope inserted through a small incision limits the overall understanding of the surgical environment. Further, current technology requires a third port to accommodate a laparoscope (camera), and each new viewpoint requires an additional incision.

In order to reduce the number of shafts and openings necessary for the surgery, instruments or sensors are placed in the body cavity and the shaft used for placement is removed. However, removing the shaft also removes an obvious channel for wires, optical fibers or the like.

SUMMARY

In an embodiment of the present disclosure, a wire guide system is provided where the system may includes a cylindrical shaft having a hollow chamber along a longitudinal axis of the cylindrical shaft, a flange disposed around the cylindrical shaft and seal disposed around the cylindrical shaft and abutting the flange. The system may also include an anchor affixed to the cylindrical shaft and having an aperture from which at least one of a sensor, a light, a camera, tissue and/or organs may be suspended therefrom and at least one cable extending from one end of the cylindrical shaft to another end of the cylindrical shaft through the hollow chamber.

The seal may have an adhesive disposed on a surface of the seal and a removable cover disposed over the adhesive. The system may also include a cap on one end of the cylindrical shaft while the other end may be tapered. The cap may be a silicone valve. The cable may be a fiber optic cable or a wire. The anchor may be attached to the cylindrical shaft via an interference fit, snap fit or magnetic coupling and configured to be manipulated around at least one axis. The hollow chamber may include a plurality of lumens.

In another embodiment, a wire guide system may be provided which includes a cylindrical shaft having a hollow chamber along a longitudinal axis of the cylindrical shaft, a flange fit disposed around the cylindrical shaft and a seal disposed around the cylindrical shaft and abutting the flange. An anchor may also be provided that is affixed to the cylindrical shaft and has an aperture from which at least one of a sensor, a light, a camera, tissue and/or organs may be suspended therefrom. A conduit within a wall of the cylindrical shaft may also be provided where the cylindrical shaft includes an internal electrical connector attached about a distal end of the cylindrical shaft, an external electrical connector attached about a proximal end of the cylindrical shaft, and the conduit extends between the internal electrical connector and external electrical connector.

The anchor may also include an electrical connector coupled to the internal electrical connector.

BRIEF DESCRIPTION OF THE DRAWINGS

The above and other aspects, features, and advantages of the present disclosure will become more apparent in light of the following detailed description when taken in conjunction with the accompanying drawings in which:

FIG. 1 is a perspective view of a cannula suitable for use with an embodiment of the present disclosure;

FIG. 2 is a cross sectional view of the cannula of FIG. 1 taken along the line 2-2;

FIG. 3 is an enlarged perspective view of a cannula suitable for use with an embodiment of the present disclosure;

FIG. 4 is an perspective view of a distal end of the cannula in accordance with another embodiment of the present disclosure;

FIG. 5 is an enlarged perspective view of the proximal end of the cannula of FIG. 3;

DETAILED DESCRIPTION

Figure 6:
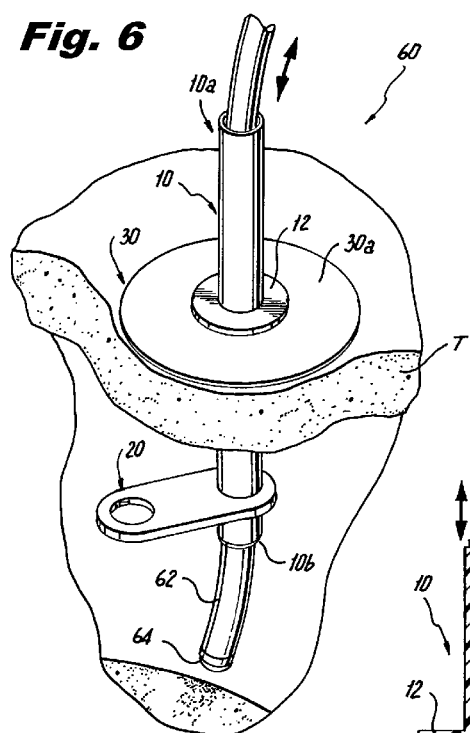
FIG. 6 is a perspective view of a wire guide according to an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user. The term "clinician" refers to any medical professional (i.e., doctor, surgeon, nurse, or the like) performing a medical procedure involving the use of embodiments described herein.

Turning to FIGS. 1-5, a cannula, shown generally as 10, has a proximal end 10a and a distal end 10b. Cannula 10 is made from polyvinyl chloride (PVC) or any other flexible material suitable for use in a body cavity or other medical applications. A flange 12 fits around cannula 10. Flange 12 and cannula 10 can be a single integrated piece or flange 12 is removably coupled to cannula 10 and can be positioned anywhere along the longitudinal length of cannula 10.

An adhesive seal 30 is disposed below and abuts flange 12 when the cannula is placed in the incision. Flange 12 may be secured to adhesive seal 30 by placing an adhesive (not shown) on proximal portion 30a (see FIG. 6) of adhesive seal 30. Distal portion 30b of seal 30 has an adhesive 32 thereon. Adhesive 32 adheres adhesive seal 30 to the skin of a patient around an incision to prevent insufflation gases from escaping the body cavity. Adhesive 32 may be any suitable biocompatible adhesive. A cover or flap 34 covers the adhesive 32 until the cannula 10 is ready to be inserted into an incision.

Distal end 10b of cannula may have a flat end as shown in FIG. 3 or distal end 10b may have a tapered end 40 (see FIG. 4). Tapered end 40 enables a clinician to insert cannula 10 into an incision relatively easier than a flat ended cannula. As shown in FIG. 5, proximal end 10a has a cap 50 that can be used to close the proximal end of chamber 14. Closing proximal end 14a of chamber 14 prevents insufflation gases from escaping a body cavity. Cap 50 may be a siliconee valve with slits 52 that allow a clinician to place objects through the valve when necessary while inhibiting insufflation gases from escaping the body cavity.

An anchor 20 may be fitted around cannula 10, by an interference fit, to suspend devices (such as lights, cameras, sensors, etc.), tissue and/or organs. As shown in FIGS. 1 and 3, anchor 20 fits around the distal end 10b of cannula 10 by fitting cannula 10 through aperture 24. A second aperture 22 is used to suspend the devices, tissue and/or organs therefrom. Although anchor 20 depicts an aperture 22 for suspending devices, anchor 20 may include a plurality of apertures for suspending one or more devices.

Figure 7:
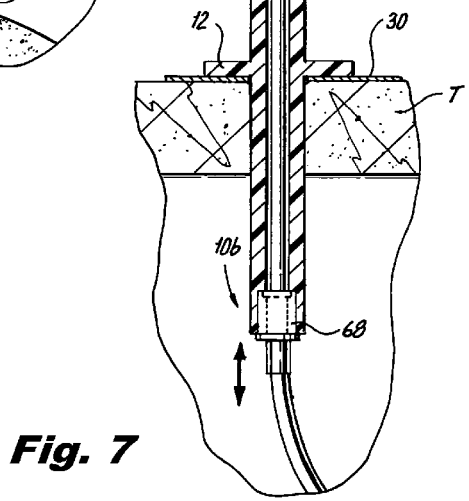
FIG. 7 is a cross-sectional view of the wire guide of FIG. 6.

Turning to FIGS. 6 and 7, a wire guide 60 according to an embodiment of the present disclosure is depicted. When a clinician is ready to use cannula 10, an incision is made in tissue "T". Distal end 10b of cannula 10 is placed through an aperture of adhesive seal 30. The clinician peels flap 34 off of adhesive 32 and inserts cannula 10 into the incision. Adhesive 32 adheres to tissue "T" of the patient providing a seal around the cannula to inhibit leakage of insufflation gases. After the cannula 10 is placed in the incision, the clinician affixes an anchor 20 to the distal end 10b of cannula 10 inside the body cavity.

As shown in FIG. 6, a cable 62 may be fed through cannula 10. Cable 62 may be a fiber optic cable having a lens or a charge-coupled device (CCD) at distal end 64. Alternatively, cable 62 may be a single wire or multiple wires having at least one sensor, light and/or digital camera at distal end 64. The proximal end of cable 62 (not shown) may be connected to a computer, monitor, or any other device capable of receiving signals, interpreting signals and displaying the interpreted signals.

As shown in FIG. 7, cannula 10 may be fitted with proximal plug 66 and distal plug 68. Plugs 66 and 68 may be made from an elastomer such as rubber or a flexible PVC material to inhibit insufflation gases from escaping the body cavity. Distal end 64 of cable 62 is fed through proximal plug 66, chamber 14 and out distal end 10b through distal plug 68.

Figure 8:
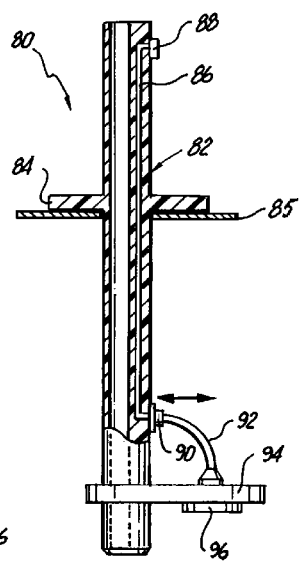
FIG. 8 is a cross sectional view of a wire guide in accordance with another embodiment of the present disclosure.

Turning to FIG. 8, a wire guide 80 according to another embodiment of the present disclosure is depicted. Similar to cannula 10, wire guide 80 has a cannula 82 with a flange 84 around cannula 82. An adhesive seal 85 is disposed below and abuts flange 84. A wire or conduit 86 is disposed within the wall of cannula 82. Conduit 86 couples a receptacle or port 88 with a receptacle or port 90. Receptacle 84 may be connected to a conduit (not shown) that is coupled to a computer, monitor and/or power source. Receptacle 90 may be coupled to a device 96 attached to anchor 94 via a wire or conduit 92. Receptacle 90 may provide power to device 96 via conduit 92 or it may transmit data from device 96 to a computer or monitor via conduit 92. Device 96 may be at least one sensor, light and/or camera that have been attached to anchor 94. Placing conduit 86 in the wall of cannula 82 increases the amount of space available in the cannula 82 for endoscopic or laparoscopic instruments while preventing such instruments from being tangled with the conduit 86.

Figure 9:
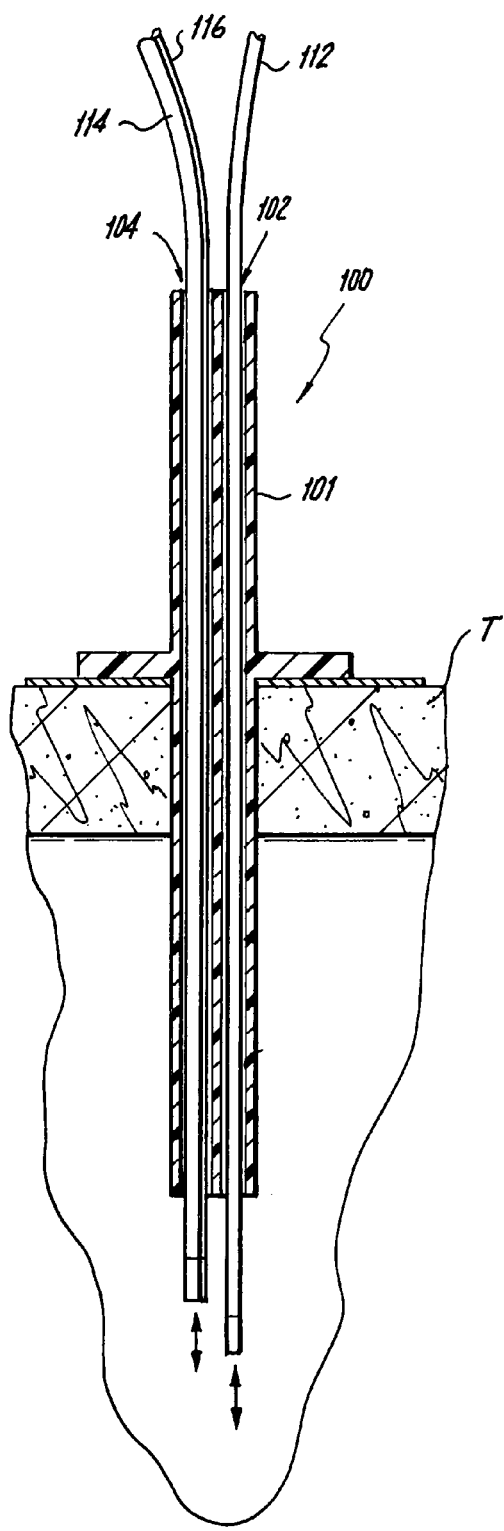
FIG. 9 is a cross sectional view of a wire guide in accordance with another embodiment of the present disclosure.

FIG. 9 depicts another example of a wire guide 100, in accordance with an embodiment of the present disclosure, having multiple chambers. As shown in FIG. 9, wire guide 100 utilizes a cannula 101 having at least two lumens 102 and 104. Although FIG. 9 depicts only two lumens, any number of lumens may be fabricated within wire guide 100. A single wire 112 may be placed through lumen 102 or multiple wires, such as wires 114 and 116, may be placed through chamber 104. By using separate lumens, wires do not tangle with each other. As such, when one wire is pulled, the other wires can stay in place. Alternatively, lumen 102 may be used for wires while lumen 104 may be used for endoscopic or laparoscopic instruments, guidance and targeting instruments or for the passage of fluids, drugs or sealants.

Figure 10:
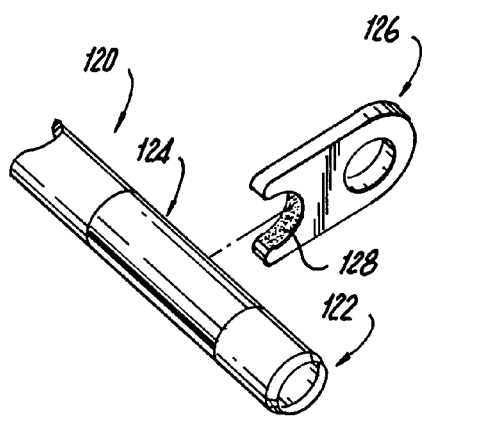
FIG. 10 is a perspective view of an anchor in accordance with another embodiment of the present disclosure.

FIGS. 10-15 depict examples of different anchors that may be used in conjunction with embodiments of the present disclosure. As shown in FIG. 10, a cannula 120 has a magnetic surface 124 at distal end 122. Anchor 126 has a magnetic surface 128 that has an opposite polarity than that of magnetic surface 124. When anchor 126 is brought in close proximity to magnetic surface 124, the opposite polarities of magnetic surfaces 124 and 128 cause anchor 126 to be magnetically coupled to cannula 120. Alternatively, anchor 126 may have a magnetic surface 128 while cannula 120 is made from metals such as iron, nickel, cobalt, certain steels and/or other alloys with magnetic properties. As such, magnetic surface 128 would be attracted and affixed to cannula 120 due to a magnetic coupling between magnetic surface 128 and the metal of cannula 120.

Figure 11:
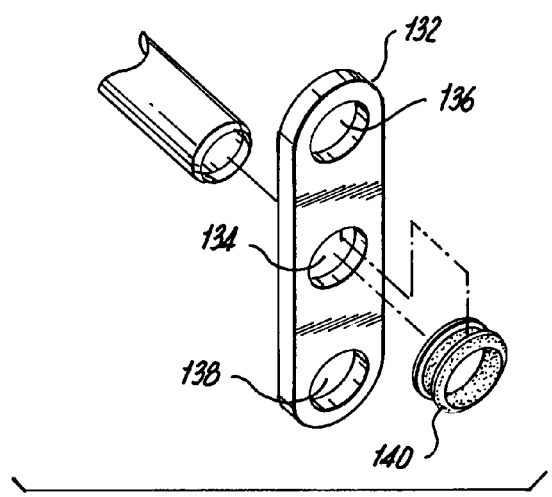
FIG. 11 is a perspective view of an anchor in accordance with another embodiment of the present disclosure.

FIG. 11 depicts another example of anchor 132 suitable for use with embodiments of the present disclosure. Anchor 132 is at least three apertures 134, 136 and 138. A grommet 140, made from an elastomer, is fitted in central aperture 134. Then cannula 130 is pushed through grommet 140 causing anchor 132 to be attached to cannula 130 via an interference fit. Apertures 136 and 138 may be used to suspend sensors, lights, cameras, tissue and/or organs therefrom.

Figure 12:
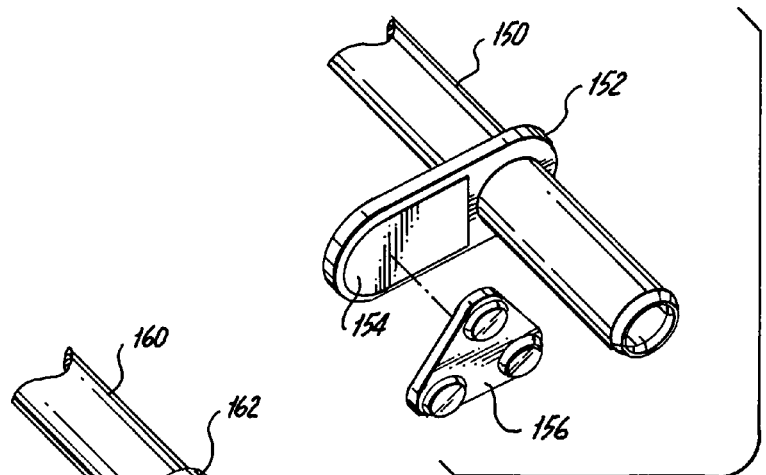
FIG. 12 is a perspective view of an anchor in accordance with another embodiment of the present disclosure.

As can be seen in FIG. 12, an anchor 152 is affixed to cannula 150 via an interference fit. Anchor 152 has a magnetic surface 154 that attracts a fixture 156. Fixture 156 may have a magnet (not shown) attached to the proximal side of fixture 156 or be made from a material with magnetic properties. Fixture 156 may have one or more sensors, one or more lights, one or more cameras or any combination thereof.

Figure 13:
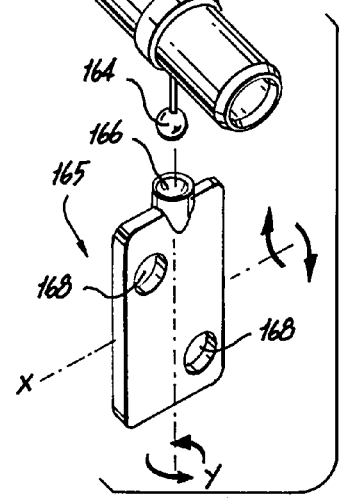
FIG. 13 is a perspective view of an anchor in accordance with another embodiment of the present disclosure.

FIG. 13, depicts another example of an anchor 165 attached to a cannula 160 utilizing a ball and socket joint. As shown in FIG. 13, a collar 162 is fitted around cannula 160. Collar 162 has a ball 164 extending outward from collar 162. Ball 164 is attached to socket 166 of anchor 165 via a snap fit. The coupling between ball 164 and socket 166 allows anchor 165 to swivel around an x-axis and rotate around a y-axis or swivel about a z-axis as marked in FIG. 13. Such movement allows a clinician to manipulate items attached to the anchor for a better view of the body cavity. Apertures 168 may be used to suspend sensors, lights, cameras, tissue and/or organs therefrom. Alternatively, ball 164 and socket 166 may be magnetically coupled to each other.

Figure 14:
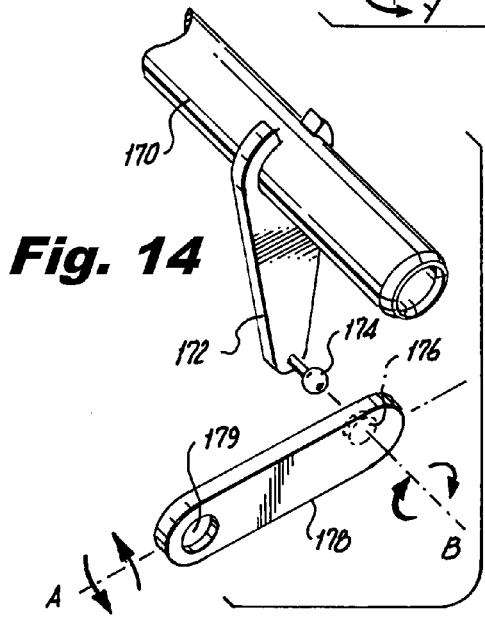
FIG. 14 is a perspective view of an anchor in accordance with another embodiment of the present disclosure.

FIG. 14 also depicts an example of an anchor 178 utilizing a ball and socket joint. As shown in FIG. 14, a flange 172 may be snapped onto cannula 170. Flange 172 has a ball 174 that snap fits into socket 176 of anchor 178 that allows anchor 178 to swivel around an A-axis and rotate around a B-axis or swivel about a C-axis as marked in FIG. 14. Aperture 179 may be used to suspend sensors, lights, cameras, tissue and/or organs therefrom.

Figure 15:
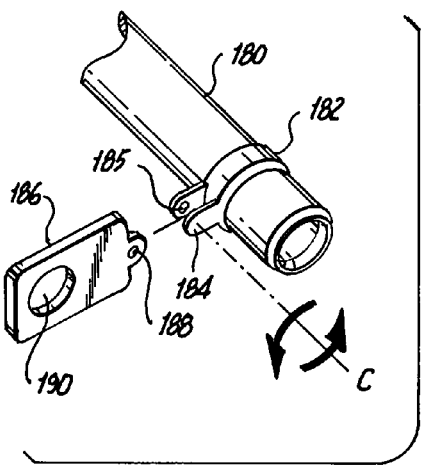
FIG. 15 is a perspective view of an anchor in accordance with another embodiment of the present disclosure.

FIG. 15 depicts an anchor 186 according to another embodiment of the present disclosure. As shown in FIG. 15, a collar 182 is fitted onto cannula 180. Collar 182 has a pair of parallel flanges 184 where each flange 184 has a recess 185. Recesses 185 receive nubs 188 of anchor 186 via a snap fit to secure anchor 186 to collar 182. Such an arrangement allows anchor 186 to swivel around a C-axis as marked in FIG. 15. Aperture 190 may be used to suspend sensors, lights, cameras, tissue and/or organs therefrom.

Figure 16:
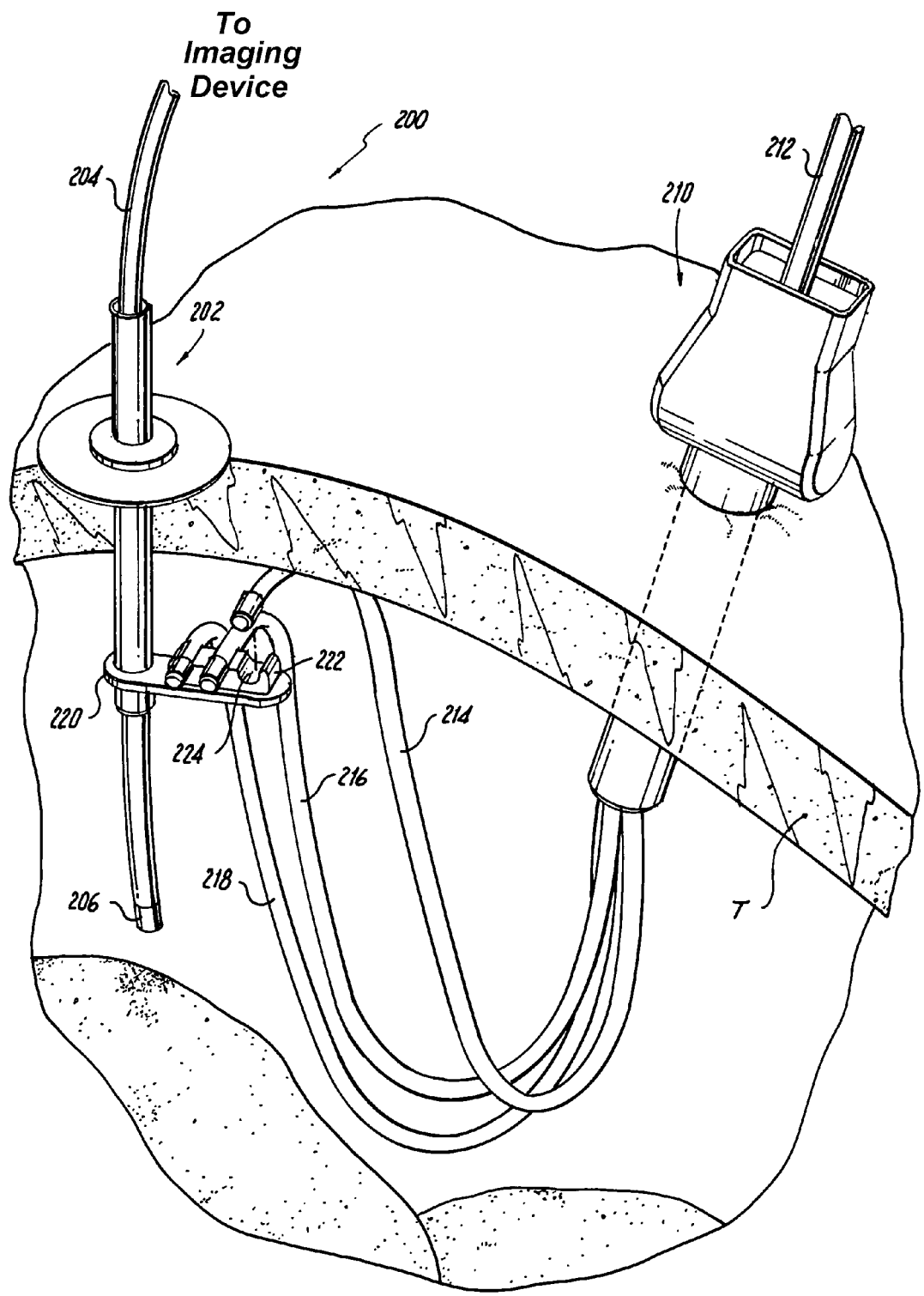
FIG. 16 is perspective view of a wire guide system in accordance with another embodiment of the present disclosure.

Turning to FIG. 16, a wire guide system 200 in accordance with an embodiment of the present disclosure is depicted. Wire guide system 200 may include a wire guide 202 similar to wire guide 60 described above. Wire guide 202 has a fiber optic cable 204 where a proximal end (not shown) of fiber optic cable 204 is connected to an imaging device and the distal end 206 of fiber optic cable 204 has a lens system or a CCD camera attached thereto. Another wire guide 210 may also be inserted through an incision in tissue "T" into the body cavity. Wire guide 210 may have a cable 212 that includes multiple wires or cables 214, 216 and 218. Each wire or cable 214, 216 and 218 may be connected to one or more power sources, computers, monitors, or any other devices capable of receiving signals, interpreting signals and displaying the interpreted signals. The distal ends of wires 214, 216 and 218 may have any number of sensors, lights and/or cameras attached thereto. An anchor 220 is affixed to wire guide 202 inside the body cavity. Anchor 220 may have a holder 222 made from rubber or any flexible PVC material. Holder 222 may have a number of recesses 224 (e.g., three as shown in FIG. 16) and wires or cable 214, 216 and 218 are snap fitted into recesses 224 to keep wires or cable 214, 216 and 218 in place.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing FIGS. are presented only to demonstrate certain examples of the disclosure. Other elements, steps, methods and techniques that are insubstantially different from those described above and/or in the appended claims are also intended to be within the scope of the disclosure.

The invention claimed is:

1. A wire guide system comprising:
    a cylindrical shaft having a hollow chamber along a longitudinal axis of the cylindrical shaft;
    a flange disposed around the cylindrical shaft;
    a seal disposed around the cylindrical shaft and abutting the flange;
    an anchor affixed to the cylindrical shaft and having an aperture from which at least one of a sensor, a light, a camera, tissue, or organs may be suspended therefrom; and
    at least one cable extending from one end of the cylindrical shaft to another end of the cylindrical shaft through the hollow chamber.

2. The wire guide system according to claim 1, wherein the seal further comprising:
    an adhesive disposed on a surface of the seal; and
    a removable cover disposed over the adhesive.

3. The wire guide system according to claim 1 further comprising a cap.

4. The wire guide system according to claim 3, wherein the cap is a silicone valve.

5. The wire guide system according to claim 1, wherein one end of the cylindrical shaft is tapered.

6. The wire guide system according to claim 1, wherein the at least one cable is a fiber optic cable or a wire.

7. The wire guide system according to claim 1, wherein the anchor is attached to the cylindrical shaft via an interference fit, a snap fit, a bayonet coupling, a latch coupling, or a magnetic coupling.

8. The wire guide system according to claim 1, wherein the anchor is configured to be manipulated around at least one axis.

9. The wire guide system according to claim 1, wherein the hollow chamber comprises a plurality of lumens.

* * * * *